United States Patent
SaNogueira et al.

(10) Patent No.: US 8,512,683 B2
(45) Date of Patent: Aug. 20, 2013

(54) EMULSION BASE FOR SKIN CARE COMPOSITIONS

(75) Inventors: James P. SaNogueira, Suffern, NY (US); Jose Huerta, Cedar Grove, NJ (US); Gerd Dahms, Duisburg (DE); Holger Seidel, Duisburg (DE); Barbara A. Donovan, Wayne, NJ (US)

(73) Assignee: Playtex Products, LLC, Shelton, CT (US)

( * ) Notice: Subject to any disclaimer, the term of this patent is extended or adjusted under 35 U.S.C. 154(b) by 1331 days.

(21) Appl. No.: 10/856,738

(22) Filed: May 28, 2004

(65) Prior Publication Data

US 2005/0152931 A1  Jul. 14, 2005

Related U.S. Application Data

(60) Provisional application No. 60/474,451, filed on May 29, 2003, provisional application No. 60/567,062, filed on Apr. 30, 2004.

(51) Int. Cl.
*A61K 8/02* (2006.01)

(52) U.S. Cl.
USPC ............................. 424/59; 424/60; 424/401

(58) Field of Classification Search
USPC .......................................................... 424/401
See application file for complete search history.

(56) References Cited

U.S. PATENT DOCUMENTS

| | | | |
|---|---|---|---|
| 4,522,807 A | 6/1985 | Kaplan | |
| 5,047,232 A | 9/1991 | Kaplan | |
| 5,229,104 A | 7/1993 | Sottery et al. | |
| 5,576,354 A | 11/1996 | Deflandre et al. | |
| 5,587,150 A | 12/1996 | Deflandre et al. | |
| 5,667,765 A | 9/1997 | Hansenne et al. | |
| 5,770,183 A | 6/1998 | Linares | |
| 5,807,561 A | 9/1998 | Guerrero | |
| 5,985,251 A | 11/1999 | Gonzenbach et al. | |
| 5,989,528 A | 11/1999 | Tanner et al. | |
| 6,033,649 A | 3/2000 | Gonzenbach et al. | |
| 6,071,501 A | 6/2000 | Robinson | |
| 6,074,630 A | 6/2000 | Devillez et al. | |
| 6,086,858 A | 7/2000 | McEleney et al. | |
| 6,238,650 B1 | 5/2001 | Lapidot et al. | |
| 6,303,149 B1 | 10/2001 | Magdassi et al. | |
| 6,338,838 B1 | 1/2002 | Berset et al. | |
| 6,368,577 B1 | 4/2002 | Kropf et al. | |
| 6,372,200 B2 | 4/2002 | Josso et al. | |
| 6,403,061 B1 | 6/2002 | Candau et al. | |
| 6,409,998 B1 | 6/2002 | Candau et al. | |
| 6,416,748 B1 | 7/2002 | Candau et al. | |
| 6,416,773 B2 | 7/2002 | Heidenfelder et al. | |
| 6,432,389 B1 | 8/2002 | Hansenne et al. | |
| 6,436,375 B1 | 8/2002 | Lapidot et al. | |
| 6,436,376 B1 | 8/2002 | Hansenne et al. | |
| 6,468,509 B2 | 10/2002 | Lapidot et al. | |
| 6,485,712 B1 | 11/2002 | Kim et al. | |
| 6,485,713 B1 | 11/2002 | Bonda et al. | |
| 6,491,902 B2 | 12/2002 | Shefer et al. | |
| 6,495,122 B2 | 12/2002 | Fankhauser et al. | |
| 6,500,411 B2 | 12/2002 | SenGupta et al. | |
| 6,511,673 B1 | 1/2003 | Chia et al. | |
| 6,521,217 B1 | 2/2003 | Luther et al. | |
| 6,562,353 B1 | 5/2003 | Breton et al. | |
| 6,664,356 B1 * | 12/2003 | Shih ........................... 526/328.5 |
| 6,696,490 B2 * | 2/2004 | Meyer et al. ................... 514/546 |
| 6,710,022 B1 * | 3/2004 | Kwetkat et al. ............... 510/119 |
| 2001/0022965 A1 | 9/2001 | Heger et al. | |
| 2001/0053348 A1 | 12/2001 | Stewart et al. | |
| 2002/0006418 A1 | 1/2002 | Kung et al. | |
| 2002/0064560 A1 | 5/2002 | Kung et al. | |
| 2002/0086039 A1 | 7/2002 | Lee et al. | |
| 2003/0129151 A1 | 7/2003 | Candau et al. | |
| 2003/0143166 A1 | 7/2003 | Heger et al. | |
| 2003/0161847 A1 | 8/2003 | Ansmann et al. | |
| 2003/0176470 A1 * | 9/2003 | Bunger et al. ................. 514/357 |
| 2003/0185772 A1 | 10/2003 | Kouzuki et al. | |
| 2003/0202948 A1 | 10/2003 | Koini et al. | |
| 2003/0219392 A1 | 11/2003 | Kung et al. | |
| 2003/0228267 A1 | 12/2003 | Aust et al. | |
| 2003/0235540 A1 | 12/2003 | Herzog | |
| 2005/0031653 A1 * | 2/2005 | Kwetkat et al. ............... 424/401 |

FOREIGN PATENT DOCUMENTS

| | | | |
|---|---|---|---|
| WO | WO01/19945 | * | 3/2001 |
| WO | WO/01/89469 | * | 5/2001 |
| WO | WO03/024412 | * | 3/2003 |

OTHER PUBLICATIONS

Sasol, http://www.warnergraham.com/products/sasol.asp (accessed Mar. 10, 2009).*
Kemira, http://www.cheshamchemicals.co.uk/kemira.htm (accessed Mar. 10, 2009).*

* cited by examiner

*Primary Examiner* — Frederick Krass
*Assistant Examiner* — Adam C Milligan
(74) *Attorney, Agent, or Firm* — Ohlandt, Greeley, Ruggiero & Perle, L.L.P.

(57) ABSTRACT

The present invention is directed to an emulsion base for formulating cosmetic and dermatological compositions. The emulsion base has particular surfactant and/or emulsifier ratios such that a wide range of compositions with varying forms and additional components can be formulated without changing the ratio or amount of the primary and/or co-surfactant/emulsifier in the emulsion base or the amount of the emulsion base in the final composition. The emulsion base can be used in a system of formulating cosmetic and dermatological compositions.

21 Claims, No Drawings

EMULSION BASE FOR SKIN CARE COMPOSITIONS

RELATED APPLICATIONS

This application claims priority to U.S. Provisional Patent Application No. 60/474,451 filed on May 29, 2003, and U.S. Provisional patent Application No. 60/567,062 filed on Apr. 30, 2004.

BACKGROUND OF THE INVENTION

1. Field of the Invention

The present invention relates to a stable and flexible emulsion base for use in formulating cosmetic and dermatological compositions. More particularly, the present invention relates to stable and flexible emulsion bases with surfactant/emulsifier ratios that allow formulation of a broad range of cosmetic and dermatological compositions, specifically suncare compositions.

2. Description of the Related Art

Cosmetic and dermatological compositions, including suncare compositions, are commercially available in various forms, such as lotions, sprays, creams, gels, milks, and the like, and are well known in the art.

Formulators of such compositions generally start by combining various components together to develop, through trial and error, a composition that is stable and has the desired properties and form. These formulations typically involve a significant amount of time and expense with each attempt at a different combination of components and concentrations of those components.

Particularly, there are difficulty-formulating compositions that are stable and have properties desired for a specific type of composition. Compositions for different end uses require different basic properties, such as affinity of the composition for the skin and ability to be waterproof. The consumers of the compositions also demand certain properties, such as a luxurious, non-oily feeling on the skin. Consumers of suncare compositions, in particular, consider many factors when purchasing a suncare product, such as, the sun protection factor (SPF), how durable the product is after applying it over the skin, the shelf life of the product, and product form (i.e., lotions, gels, creams, and sprays). Another important and influential property of a suncare product considered by a consumer is how the product dispenses and how well the product spreads over the skin. Typically, consumers want a suncare product that does not drip and/or run from the dispenser orifice, from the hand during application, or once applied to the skin. Balancing these properties in a composition that is also stable over time can require a multitude of costly trials before a suitable final formulation is obtained.

This difficulty is evident in the formulation of suncare compositions, especially those having UV absorbing or blocking active agents. Many of the suncare active agents, such as avobenzone, are known to pose particular problems in formulating stable compositions that also have desirable aesthetic and skin feel properties. Furthermore, the addition of waterproofing agents to compositions is often highly desirable. This is the case with suncare products where the consumer expects UV protection to last for considerable time periods despite the typical use of suncare products in outdoor activities that involve either water or perspiration. However, the addition of waterproofing agents is also known to produce difficulties in formulating stable compositions.

Attempts have been made to provide base formulations to which active agents, typical excipients, and emollients can be easily added to form cosmetic and dermatological compositions with decreased formulation and production expense. However, designing a base formulation that is stable, while providing the flexibility to adjust the base formulation and/or produce final compositions that have properties over wide ranges, is very difficult. A particular difficulty arises in balancing the types and concentrations of emulsifiers and surfactants in the base formulation needed to provide the desired properties in an oil-in-water (O/W) emulsion. Stability of such O/W emulsions can typically be enhanced by increasing the viscosity, which can be achieved by the addition of hydrophilic compounds such as certain emulsifiers and gums. However, finding the proper balance between greater stability and compositions that have unworkable thicknesses has heretofore not been satisfactorily achieved. A base formulation that also allows for ease and flexibility in the addition of waterproofing agents engenders further difficulty in design.

SUMMARY OF THE INVENTION

It is an object of the present invention to provide a flexible and stable emulsion base for formulating stable compositions including suncare, cosmetic, and dermatological compositions.

It is another object of the present invention to provide a flexible and stable emulsion base that allows the formulation of a broad range of product forms without changing the ratio or amount of the primary surfactant/emulsifier and/or co-surfactant/emulsifier.

It is still another object of the present invention to provide such an emulsion base that can be formulated easily with a broad range of active agents, excipients, and emollients without changing the ratio or amount of the primary surfactant/emulsifier and/or co-surfactant/emulsifier.

It is still yet another object of the present invention to provide such an emulsion base that can be formulated easily with waterproofing agents without changing the ratio or amount of the primary surfactant/emulsifier and/or co-surfactant/emulsifier.

It is a further object of the present invention to provide a stable and flexible system using such an emulsion base.

It is still a further object of the present invention to provide such a system that allows changes in viscosity of the formulated composition without changes in the emulsion base and/or the amount of the emulsion base present in the total composition.

It is yet a further object of the present invention to provide a method of formulating a composition, including a suncare composition, having a stable and flexible emulsion base that does not change the ratio or amount of the primary surfactant/emulsifier and/or co-surfactant/emulsifier.

These and other foregoing objects and advantages, of the present invention are achieved, in brief summary, by an emulsion base that is stable and has the flexibility to allow the formulation of a broad range of product forms without changing the ratio or amount of the primary surfactant/emulsifier and/or co-surfactant/emulsifier. The present invention also provides a system of using an emulsion base to formulate a broad range of compositions without changing the ratio or amount of the primary surfactant/emulsifier and/or co-surfactant/emulsifier. The present invention further provides suncare compositions formulated using such an emulsion base and/or system.

DETAILED DESCRIPTION OF THE INVENTION

It has been unexpectedly found that a flexible and stable system including an emulsion base, or base chassis, for use in the formulation of stable compositions, including cosmetic, dermatological, and/or suncare compositions, can be designed with particular ratios of one or more surfactants and/or emulsifiers.

An emulsion base of the present invention is a formulation having one or more primary surfactants/emulsifiers and one or more co-surfactants/emulsifiers. The one or more primary surfactants is a material that reduces interfacial tensions by having a dual functionality (hydrophobic portion and hydrophilic portion) allowing it to form an emulsion. Examples of suitable primary surfactants for use in an emulsion base of the present invention include, but are not limited to, CERALUTION® F, ceteareth-20, lauryl glucoside, sodium dicocoylethylenediamine PEG-15 sulfate, sodium lauroyl sarcosinates, or any combinations thereof. CERALUTION® F is available from Sasol and includes sodium dicocoylethylenediamine PEG-15 sulfate and sodium lauroyl sulfate.

The one or more co-surfactants is a material that assists the primary surfactant by improving the packing at the primary surfactant interface and stabilizing the emulsion. The one or more co-surfactants preferably have an HLB value equal to or less than about 5. At this HLB value, a lamellar gel network is pre-built that when combined with a hydrophilic surfactant, that has a high HLB, renders the final emulsion. Examples of suitable cosurfactants for use in an emulsion base of the present invention include, but are not limited to, CERALUTION® H, BIOBASE® EP, glyceryl monostearate, solid fatty alcohols, sorbitan trioleate, fatty esters, glyceryl stearate, or any combinations thereof. CERALUTION® H is available from Sasol and includes behenyl alcohol, glyceryl stearate, glyceryl stearate citrate, and sodium dicocoylethylenediamine PEG-15 sulfate. BIOBASE® EP is available from Tri-K and includes glyceryl stearate, cetearyl alcohol, sodium lauroyl lactylate, and lecithin.

It has been unexpectedly found that combining the one or more primary surfactants and the one or more co-surfactants in certain ratios provides a stable emulsion base, which can be used to formulate a broad range of product forms using a broad range of additional components, without changing the ratio of the primary surfactants and/or co-surfactants and/or changing the amount of the emulsion base in the total amount of the final formulated composition. As a result, a composition can be formulated without undue experimentation, reducing the time and expense associated with the formulation. In addition, it has been found that the emulsion base permits the inclusion of any known ester therein.

The ratio of the one or more primary surfactants to the one or more co-surfactants in an emulsion base of the present invention ranges from about 1:3.75 to about 3.75:1 In one embodiment of the present invention, the ratio of the one or more primary surfactants to the one or more co-surfactants in an emulsion base of the present invention is from about 1:2.67 to about 3:1. In another embodiment of the present invention, the ratio is about 2.13:1 of one or more primary surfactants to one or more co-surfactants. In yet another embodiment of the present invention, the ratio is about 3:1 of one or more primary surfactants to one or more co-surfactants. In still yet another embodiment of the present invention, the ratio is about 1:2.67 of one or more primary surfactants to one or more co-surfactants. Once an acceptable ratio is chosen, different compositions can be formed having varying properties from an emulsion base of the present invention without changing the chosen ratio of one or more primary surfactants to one or more co-surfactants.

An emulsion base of the present invention itself may have the following components: diluent, thickener, emollient, humectant, preservative, solvent, or any combinations thereof. Preferably, an emulsion base of the present invention itself is formulated with one or more primary surfactants, one or more co-surfactants, one or more diluents, one or more thickeners, one or more emollients, one or more humectants, and one or more preservatives.

One or more diluents may be present in an emulsion base of the present invention. Preferably, the diluent is water. The diluent may be present in an emulsion base of the present invention in an amount from about 39 wt. % to about 87 wt. %, preferably from about 42 wt. % to about 70 wt. %, most preferably about 44 wt. % to about 68 wt. % of the total weight of the emulsion base itself.

One or more emollients may be present in an emulsion base of the present invention. Examples of emollients that can be used in an emulsion base of the present invention include, but are not limited to, cocoglyceride, cyclomethicone, dimethicone, dicapryl maleate, caprylic/capric triglyceride, isopropyl myristate, octyl stearate, mineral oil, lanolin oil, coconut oil, cocoa butter, olive oil, avocado oil, aloe extracts, jojoba oil, castor oil, fatty acid such as oleic and stearic, fatty alcohol such as cetyl and hexadecyl, diisopropyl adipate, hydroxybenzoate esters, benzoic acid ester of $C_9$-$C_{15}$ alcohols, isononyl iso-nonanoate, alkane such as mineral oil, silicone such as dimethyl polysiloxane, ether such as polyoxypropylene butyl ether and polyoxypropylene cetyl ether, $C_{12}$-$C_{15}$ alkyl benzoate, octyldodecyl neopentanoate, PEG-7 methyl ether, di-PPG-3 myristyl ether adipate, LEXFEEL 350 (dipentaerythritol hexa $C_{5-9}$ acid esters), LEXGARD O (caprylyl glycol) that is available from Inolex, CRODAMOL PMP (PPG-2 myristyl ether propionate) that is available from Croda or any combinations thereof. Preferably, the emollient of an emulsion base of the present invention is $C_{12}$-$C_{15}$ alkyl benzoate, PEG-7 methyl ether, or any combinations thereof.

It is noted that the emulsion base can include sunscreen boosters and/or photostabilizers. For example, PEG-7 methyl ether acts as a SPF booster. LEXOGARD O acts as both a sunscreen photostabilizer and booster.

The emollient may be present in an emulsion base of the present invention in an amount about 14 wt. % to about 45 wt. %, preferably about 18 wt. % to about 33 wt. %, and more preferably about 21 wt. % to about 28 wt. % of the total weight of the emulsion base itself.

One or more thickeners may be present in an emulsion base of the present invention. Examples of thickeners that can be used in an emulsion base of the present invention include, but are not limited to, acetamide MEA, acrylamide copolymer, acrylates copolymer, acrylates/steareth-20 methacrylate copolymer, acrylates/beheneth-25 methacrylate copolymer, PEG-150/decyl alcohol/SMDI copolymer, PVP, PVM/MA decadiene crosspolymer, carbomer, PEG crosspolymer, acrylates/palmeth-25 acrylates copolymer, polysaccharide, polyether-1, sodium magnesium silicate, bentonite, trihydroxystearin, hydroxy stearate, aluminum-magnesium hydroxide stearate, acacia gum, xanthan gum, or any combinations thereof. Preferably, the thickeners of an emulsion base of the present invention are Acacia gum, xanthan gum, or any combinations thereof.

The one or more thickeners may be present in an emulsion base of the present invention in an amount from about 0.05 wt. % to about 3 wt. %, preferably from about 0.1 wt. % to about 2 wt. %, and more preferably about 0.15 wt. % to about 1.7 wt. % of the total weight of the emulsion base itself.

One or more humectants may be present in an emulsion base of the present invention. Examples of humectants that can be used in an emulsion base of the present invention include, but are not limited to, glycerin, propylene glycol, butylene glycol, sorbitol, PEG-4, or any combinations thereof. Preferably, the humectant of an emulsion base of the present invention is glycerin.

The one or more humectants may be present in an emulsion base of the present invention in an amount about 3 wt. % to about 11 wt. %, preferably about 4 wt. % to about 8 wt. %, most preferably about 5 wt. % to about 7 wt. %, of the total weight of the emulsion base itself.

One or more preservatives may be present in an emulsion base of the present invention. The one or more preservatives protect the emulsion base and the compositions formulated from the emulsion base from microbial contamination and/or oxidation. As such, the preservative can include an antioxidant. Examples of preservatives that can be used in an emulsion base of the present invention include, but are not limited to, diazolidinyl urea, iodopropynyl butylcarbamate, DMDM hydantoin, iodipropynyl butylcarbamate, chloromethylisotiazolinone, methylisothiazolinone, methyldibromo glutaronitrile, vitamin E and its derivatives including vitamin E acetate, vitamin C, butylated hydroxytoluene (BHT), butylparaben, ethylparaben, methylparaben, propylparaben, phenoxyethanol, or any combinations thereof. In one embodiment, the preservative is a combination of DMDM hydantoin and iodopropynyl butylcarbamate sold under the tradename GLYDANT PLUS® by Lonza. In another embodiment, the preservative is a combination of methyldibromo glutaronitrile, methylchloroisothiazolinone, methylisothiazolinone, and phenoxyethanol sold under the tradename EUXYL® K727 by Schulke and Mayr GMBH & Co. KG.

The one or more preservatives may be present in an emulsion base of the present invention in an amount about 0.1 wt. % to about 2 wt. %, preferably about 0.5 wt. % to about 1.5 wt. %, most preferably about 1 wt. % to about 1.3 wt. %, of the total weight of the emulsion base itself.

A preferred example of the emulsion base is set forth in Table 1.

TABLE 1

Emulsion Base Example A

| Emulsion Base | Weight % of Emulsion Base |
| --- | --- |
| Water | 43.94 |
| Acacia gum | 1.46 |
| $C_{12-15}$ alkyl benzoate | 28.23 |
| Glycerin | 6.98 |
| CERALUTION ® F | 4.66 |
| CERALUTION ® H | 3.78 |
| BIOBASE ® EP | 0.87 |
| Ceteareth-20 | 9.31 |
| Xanthan gum | 0.17 |
| GLYDANT ® Plus | 0.60 |

CERALUTION ® F is available from Sasol and includes sodium dicocoylethylenediamine PEG-15 sulfate and sodium lauroyl sulfate.
CERALUTION ® H is available from Sasol and includes behenyl alcohol, glyceryl stearate, glyceryl stearate citrate, and sodium dicocoylethylenediamine PEG-15 sulfate.
BIOBASE ® EP is available from Tri-K and includes glycerin stearate, cetearyl alcohol, sodium lauroyl lactylate, and lecithin.
GLYDANT ® Plus is available from Lonza and includes DMDM hydantoin and iodopropynyl butylcarbamate.

Another example of an emulsion base of the present invention is set forth in Table 2.

TABLE 2

Emulsion Base Example B

| Emulsion Base | Weight % of Emulsion Base |
| --- | --- |
| Water | 67.35 |

TABLE 2-continued

Emulsion Base Example B

| Emulsion Base | Weight % of Emulsion Base |
| --- | --- |
| Glycerin | 5.63 |
| Lauryl glucoside | 5.75 |
| Sodium Lauroyl Sarcosinate | 2.25 |
| CERALUTION ® H | 3.05 |
| BIOBASE ® EP | 0.7 |
| PEG-7 methyl ether | 14.08 |
| Xanthan gum | 0.23 |
| EUXYL ® K727 | 0.94 |

EUXYL K727 is available from Schulke and Mayr GMBH & Co. KG and includes methyldibromo glutaronitrile, methylchloroisothiazolinone, methylisothiazolinone, and phenoxyethanol.

Yet another example of an emulsion base of the present invention is set forth in Table 3.

TABLE 3

Emulsion Base Example C

| Emulsion Base | Weight % of Emulsion Base |
| --- | --- |
| Water | 61.30 |
| Glycerin | 5.13 |
| Lauryl glucoside | 5.24 |
| Sodium Lauroyl Sarcosinate | 2.05 |
| CERALUTION ® H | 2.78 |
| BIOBASE ® EP | 0.64 |
| PEG-7 methyl ether | 21.37 |
| Xanthan gum | 0.21 |
| GLYDANT ® PLUS | 1.28 |

Still yet another example of an emulsion base of the present invention is set forth in Table 4.

TABLE 4

Emulsion Base Example D

| Emulsion Base | Weight % Emulsion Base |
| --- | --- |
| Water | 62.75 |
| Glycerin | 6.72 |
| PEMULEN ® TR-2 | 0.56 |
| Sodium Lauroyl Sarcosinate | 1.68 |
| CERALUTION ® H | 3.64 |
| BIOBASE ® EP | 0.84 |
| PEG-7 methyl ether | 22.41 |
| Xanthan gum | 0.28 |
| EUXYL ® K727 | 1.12 |

PEMULEN ® TR-2 is available from Noveon and includes acrylates/$C_{10-30}$ alkyl acrylate crosspolymer.

Testing has shown these examples of the emulsion base of the present invention to be stable at higher temperatures, e.g. 40° C. for three months and 50° C. for one month.

These examples of the stable emulsion base of the present invention provide superb flexibility in the ability to formulate a wide range of product forms including a wide range of additional components. The emulsion base provides a stable platform for formulating compositions that have desirable properties, including, for example, a luxurious skin feel and improved skin affinity.

The use of the primary and co-surfactant in the specified ratios provides a system that allows the formulator to simply add additional components to a sample of the emulsion base to produce a stable composition. There are no specific requirements for the additional components that may be selected from the typical components used to formulate cosmetic and dermatological compositions. Examples of additional components that may be formulated with an emulsion base of the present invention include, but are not limited to, sunscreen agent; secondary surfactant; secondary emollient; skin-feel additive; moisturizing agent; film former/waterproofing agent; bio-active (functional) ingredient; pharmaceutical ingredient; pH adjuster/chelating agent; secondary preservative; antimicrobial; secondary humectant; rheology modifying agent; one or more fragrances; colorants; plant extracts; absorbents; salicylic acid; alpha and beta hydroxy acids; vitamins including vitamins A, C, and E and their derivatives; or any combinations thereof.

The formulator can easily change compositions by simply changing the type and amount of additional components. Further, the formulator can easily change the emulsion base so long as the emulsion base retains the desired ratio of primary surfactant to co-surfactant. The formulator can use the same emulsion base to formulate a wide range of compositions having various viscosities, SPF values, levels of active agent, levels of waterproofing agent, or levels of other desired additional components. Additional aqueous components can be added to the emulsion base by simple mixing. Additional oil components can be added to the emulsion base with the addition of energy and/or high sheer. This is done to ensure desired particle sizes. Additional components can be easily added to the emulsion base after the emulsion base has been formulated. Alternatively, additional components can be added to the oil phase of the emulsion base and to the aqueous phase of the emulsion base prior to combination.

The formulation of various compositions having different properties can be done with or without changing the amount of the emulsion base present in the final composition. Thus, a static amount of an emulsion base of the present invention can be used to formulate compositions that have various properties. Typically, the amount of an emulsion base of the present invention that can be used to formulate compositions is about 10 wt. % to about 25 wt. % of the total weight of the composition formulated therewith. Preferably, the amount of an emulsion base of the present invention is about 15 wt. % to about 25 wt. % of the total weight of the formulated composition. More preferably, the amount of an emulsion base of the present invention is about 17 wt. % to about 23.5 wt. % of the total weight of the formulated composition.

Formulating one or more waterproofing agents with a suncare composition is highly desirable, yet poses stability problems in balancing the waterproofing agent with the emulsion system and other components of the composition. High surfactant or emulsifier content raises this difficulty. After a sunscreen emulsion is applied to the skin, emulsifier components tend to become part of the oil phase, which remains on the skin. If there is excess emulsifier unbound in the oil phase, it more readily reforms an emulsion when water comes in contact with the skin and, thus, allows for oil phase active ingredients to be washed off the skin. Having a minimum amount of emulsifier necessary to maintain a given oil phase in a sunscreen composition minimizes this wash off effect and keeps the sunscreen actives on the skin.

Further, with less emulsifier, it is possible to use less waterproofing agent/film forming compound or to use a less efficient waterproofing agent/film forming compound than would otherwise be necessary to achieve a certain level of waterproofing. Less efficient waterproofing agent/film forming compounds are also less expensive than the higher efficiency components. The emulsion base of the present invention overcomes these difficulties.

The one or more film former/waterproofing agents is a hydrophobic material that imparts film forming and waterproofing characteristics to the emulsion. It has been unexpectedly found that the emulsion base of the present invention provides a stable base for formulating the one or more film former/waterproofing agents in ratios of 0.1:7 to 7:0.1 film former/waterproofing agent to total amount of surfactants/emulsifiers in the total composition.

Suitable film former/waterproofing agent for use in the compositions of the present invention include, but is not limited to, acrylates/$C_{12-22}$ alkylmethacrylate copolymer, $C_{30-38}$ olefin/isopropyl maleate/MA copolymer, polyethylene, waxes, VP/dimethiconylacrylate/polycarbamyl polyglycol ester, butylated PVP, PVP/hexadecane copolymer, PVP/eicosene copolymer, tricontanyl PVP, Brassica Campestris/Aleuritis Fordi Oil copolymer, aminofunctional silicones, decamethyl cyclopentasiloxane (and) trimethylsiloxysilicate, octadecene/MA copolymer, or any combinations thereof.

In one embodiment, the one or more film former/waterproofing agents is acrylates/$C_{12-22}$ alkylmethacrylate copolymer sold under the tradename Allianz OPT® by ISP. In another embodiment, the one or more film former/waterproofing agents is octadecene/MA copolymer sold under the tradename PA-18 by Chevron Philips.

One or more film formers/waterproofing agents may be present in the compositions of the present invention in an amount about 0.1 wt. % to about 5 wt. % of the total weight of the composition. Preferably, the one or more film formers/waterproofing agents are present in the compositions of the present invention in an amount about 1 wt. % to about 3 wt. % of the total weight of the composition. More preferably, the one or more film formers/waterproofing agents are present in the compositions of the present invention in an amount about 1.5 wt. % to about 2.5 wt. % of the total weight of the composition.

Furthermore, the emulsion base overcomes the inherent instability of formulating compositions with particular sunscreen agents, for example avobenzone or octyl methoxycinnamate. The emulsion base provides a stable platform for the formulation of compositions having one or more sunscreen agents. These compositions are stable and have aesthetic and skin feel properties that are desirable to the consumer.

When it is desired to formulate a suncare composition, one or more sunscreen agents may be formulated with the emulsion base and system of the present invention. The one or more sunscreen agents that can be used in the present invention must be capable of absorbing or blocking the harmful effects of ultraviolet radiation. In addition, they must be non-toxic and non-irritating when applied to the skin. Suitable sunscreen agents that may be used in formulating a suncare composition include, but are not limited to, para-aminobenzoic acid (PABA), butyl methoxydibenzoylmethane (avobenzone), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate (octinoxate), octyl salicylate (octisalate), PABA, 2-phenyl-benzimidazole-5-sulphonic acid, triethanolamine salicylate, 3-(4-methylbenzylidene)-camphor, red petrolatum, zinc oxide, titanium dioxide, 3-(4-methylbenzyldine)boran-2-one (methylbenzindinecamphor), benzotriazole, phenylbenzimidazole-5-sulfonic acid, methylene bis-benzotrizolyl tetramethylbutyl phenol, or any combinations thereof.

The one or more sunscreen agents may be present in compositions formulated according to the present invention at about 1 wt. % to about 40 wt. % of the total weight of the composition. The amount of sunscreen agent in the composition will vary in the above range depending on the sun protection factor (SPF) desired. Typically, the higher the SPF, the greater the total amount of sunscreen agent. In one embodiment of the present invention, the one or more sunscreen agents are included at about 2 wt. % to about 35 wt. % of the total weight of the composition to achieve a SPF of about 2 to about 50. In another embodiment of the present invention, the one or more sunscreen agents are included in an amount about 4 wt. % to about 24 wt. % of the total weight of the composition to achieve a SPF value of about 4 to about 30. In yet another embodiment of the present invention, the one or more sunscreen agents are present in an amount about 16 wt. % to about 24 wt. % of the total weight of the composition.

The emulsion base of the present invention provides a stable platform for formulating waterproof sunscreen compositions, while also maintaining the ability to contain high levels of oil phase within the emulsion. The emulsion base is stable using a broad range of oil phase volume. Suitable ranges for the oil phase volume of the composition are about 5% to about 45% by volume of the total composition.

Compositions formulated according to the present invention may include one or more secondary rheology modifying agents. Such secondary rheology modifying agents may be present in addition to any rheology modifying agents or thickeners in the emulsion base itself in order to further modify the aesthetics of the final composition. Suitable secondary rheology modifying agents for use in formulating compositions according to the present invention include, but are not limited to, one or more polymeric emulsifiers, thickening agents, synthetic and natural gum or polymer products, polysaccharide thickening agents, associative thickeners, rheological additives and/or stabilizers, oil-thickening agents, or any combinations thereof.

Preferably, the one or more secondary rheology modifying agents for use in compositions formulated according to the present invention include, but are not limited to, acrylates crosspolymer, acrylates/$C_{10-30}$ alkylacrylate crosspolymer, polyacrylic acid, sodium polyacrylate, polyacrylate, acrylates/vinyl ester copolymer, PVP/decene copolymer, styrene/MA copolymer, acetamide MEA, acrylamides copolymer, acrylates copolymer, acrylates/steareth-20 methacrylate copolymer, acrylates/beheneth-25 methacrylate copolymer, PEG-150/decyl alcohol/SMDI copolymer, PVP, PVM/MA decadiene crosspolymer, carbomer, PEG crosspolymer, acrylates/palmeth-25 acrylates copolymer, polysaccharide, polyether-1, sodium magnesium silicate, bentonite, trihydroxystearin, hydroxy stearate, aluminum-magnesium hydroxide stearate, acacia gum, xanthan gum, microcrystalline cellulose, cellulose gum, or any combinations thereof. More preferably, the one or more secondary rheology modifying agents are microcrystalline cellulose, cellulose gum, acrylates/$C_{10-30}$ alkylacrylate crosspolymer, or any combinations thereof.

The amount of the one or more secondary rheology modifying agents that may be present in composition formulated according to the present invention is about 0.01 wt. % to about 10 wt. % of the total weight of the composition. Preferably, the one or more secondary rheology-modifying agent is present in an amount about 0.1 wt. % to about 5 wt. % of the total weight of the composition. More preferably, the one or more secondary rheology-modifying agent is present in an amount about 0.4 wt. % to about 1.5 wt. % of the total weight of the composition.

Compositions formulated according to the present invention may also include one or more secondary diluents. The one or more secondary diluents are in addition to any diluents present in the emulsion base itself. Suitable secondary diluents include, but are not limited to, water, glycol, or any combinations thereof. Preferably, the additional diluent is water.

The one or more secondary diluent is present in compositions formulated according to the present invention in an amount about 40 wt. % to about 90 wt. %, preferably about 45 wt. % to about 75 wt. %, and more preferably about 47 wt. % to about 51 wt. %, of the total weight of the composition.

Compositions formulated according to the present invention may include one or more secondary emollients. The one or more secondary emollients are in addition to any emollients present in the emulsion base itself. Examples of suitable secondary emollients include, but are not limited to cocoglyceride, cyclomethicone, dimethicone, dicapryl maleate, caprylic/capric triglyceride, isopropyl myristate, octyl stearate, mineral oil, lanolin oil, coconut oil, cocoa butter, olive oil, avocado oil, aloe extract, jojoba oil, castor oil, fatty acid such as oleic and stearic, fatty alcohol such as cetyl and hexadecyl, diisopropyl adipate, hydroxybenzoate esters, benzoic acid ester of $C_9$-$C_{15}$ alcohols, isononyl iso-nonanoate, alkane such as mineral oil, silicone such as dimethyl polysiloxane, ether such as polyoxypropylene butyl ether and polyoxypropylene cetyl ether, $C_{12}$-$C_{15}$ alkyl benzoate, octyldodecyl neopentanoate, di-PPG-3 myristyl ether adipate, dipentaerythritol hexa $C_{5-9}$ acid ester, tribehenin, cetyl palmitate, or any combinations thereof. Preferably, the one or more secondary emollients are octyldodecyl neopentanoate, $C_{12}$-$C_{15}$ alkyl benzoate, di-PPG-3 myristyl ether adipate, dipentaerythritol hexa $C_{5-9}$ acid ester, tribehenin, cetyl palmitate, or any combinations thereof.

The one or more secondary emollients may be present in compositions formulated according to the present invention in an amount about 0.1 wt. % to about 30 wt. % of the total weight of the composition. Preferably, the one or more secondary emollients are present in an amount about 1 wt. % to about 20 wt. % of the total weight of the composition. More preferably, the one or more secondary emollients are present in an amount about 5 wt. % to about 10 wt. % of the total weight of the composition.

The pH of the compositions of the present invention may be adjusted by one or more pH adjusters and/or chelating agents. For example, sodium hydroxide, triethanolamine, EDTA salt, or any combinations thereof, are suitable pH adjusters/chelating agents that may be included in compositions formulated according to the present invention. Preferably, the pH adjuster/chelating agent is triethanolamine, disodium EDTA, or any combinations thereof.

An effective amount of a pH adjuster and/or chelating agent is included to adjust the pH of the final compositions to about 3 to about 9. Preferably, the pH is adjusted to about 5 to about 8, and more preferably about 6 to about 7.

One or more secondary humectants may be used in the compositions of the present invention. The one or more secondary humectants are in addition to any humectant present in the emulsion base itself. Suitable secondary humectants include, but are not limited to, glycerin, propylene glycol, butylene glycol, sorbitol, PEG-4, aloe, or any combinations thereof. Preferably, the one or more secondary humectants is aloe.

One or more secondary humectants may be included in the compositions of the present invention in an amount about 0.01 wt. % to about 15 wt. % of the total weight of the composition. Preferably, the one or more secondary humectants are present in an amount about 0.01 wt. % to about 5 wt. % of the total weight of the composition. More preferably, the one or more secondary humectants are present in an amount about 0.05 wt. % of the total weight of the composition.

One or more secondary preservatives may be formulated in the compositions of the present invention. The one or more secondary preservatives are in addition to any preservative in the emulsion base itself. The one or more secondary preservatives may be present in the compositions formulated according to the present invention to provide additional preservative, antioxidant, and/or antimicrobial activity. Examples of secondary preservatives include, but are not limited to, diazolidinyl urea, iodopropynyl butylcarbamate, DMDM hydantoin, iodipropynyl butylcarbamate, chloromethylisothiazolinone, methylisothiazolinone, vitamin E and its derivatives including vitamin E acetate, vitamin C, butylated hydroxytoluene (BHT), butylparaben, ethylparaben, methylparaben, propylparaben, phenoxyethanol, or any combinations thereof. Preferably, the one or more secondary preservatives are BHT, tocopheryl acetate, DMDM hydantoin, iodopropynyl butylcarbamate, methyldibromo glutaronitrile, or any combinations thereof.

The one or more secondary preservatives may be present in an amount about 0.01 wt. % to about 2 wt. % of the total weight of the composition. Preferably, one or more secondary preservatives are present in an amount about 0.1 wt. % to about 1.5 wt. % of the total weight of the composition. More preferably, the one or more secondary preservatives may be present in an amount about 0.1 wt. %.

The emulsion base and system of the present invention can be used in the formulation of compositions in a broad range of product forms. Examples of product forms that may be obtained using the emulsion base and system include cream, lotion, spray, gel, and milk.

The emulsion base itself and compositions formulated therefrom may be dispensed from a variety of containers. Examples of suitable containers for dispensing include tube, bottle, jar, and spray devices.

The emulsion base itself can be formulated using ordinary, simple equipment and does not require major laboratory alteration or specialized equipment.

The emulsion base may be used in a method of formulating cosmetic and dermatological compositions. The method includes providing an emulsion base according to the present invention and formulating with the emulsion base additional components to provide a desired composition with desired properties. Alternatively, the method includes formulating the aqueous additional components with the aqueous phase of the emulsion base, formulating the oil phase additional components with the oil phase of the emulsion base, and combining the two phases, optionally with the addition of further components thereafter.

An example of a spray sunscreen composition formulated with an emulsion base of the present invention is set forth in Table 5.

TABLE 5

Spray Sunscreen Composition

| Emulsion Base | Phase (Aqueous or Oil) | Weight % of Composition |
|---|---|---|
| Water | A | 7.55 |
| Acacia gum and/or Xanthan gum | A | 0.25 |
| $C_{12-15}$ alkyl benzoate | O | 4.88 |
| Glycerin | A | 1.2 |
| CERALUTION ® F | A | 0.8 |
| CERALUTION ® H | O | 0.65 |
| BIOBASE ® EP | O | 0.15 |
| Ceteareth-20 | O | 1.6 |
| GLYDANT PLUS ® | A | 0.1 |
| Water | A | 49.37 |
| Octinoxate | O | 7.5 |
| Oxybenzone | O | 6 |

TABLE 5-continued

Spray Sunscreen Composition

| Emulsion Base | Phase (Aqueous or Oil) | Weight % of Composition |
|---|---|---|
| Octisalate | O | 5 |
| Avobenzone | O | 3 |
| Octocrylene | O | 2.5 |
| Acrylates/$C_{12-22}$ alkylmethylacrylate copolymer | A | 2.5 |
| Octyldodecyl neopentanoate and/or $C_{12-15}$ alkyl benzoate | O | 5 |
| Microcrystalline cellulose and cellulose gum and/or acrylates/$C_{10-30}$ alkyl acrylate crosspolymer | A | 1.1 |
| Triethanolamine | A | 0.3 |
| Disodium EDTA | A | 0.1 |
| Aloe | A | 0.05 |
| BHT and/or tocopheryl acetate | O | 0.1 |
| GLYDANT PLUS ® | A | 0.3 |
| TOTAL: | | 100 |

Another example of a spray sunscreen composition formulated with an emulsion base of the present invention is set forth in Table 6.

TABLE 6

Spray Sunscreen Composition

| Emulsion Base | Phase (Aqueous or Oil) | Weight % of Composition |
|---|---|---|
| Water | A | 9.55 |
| Acacia gum and/or xanthan gum | O | 0.28 |
| $C_{12-15}$ alkyl benzoate | A | 4.85 |
| Glycerin | A | 1.2 |
| CERALUTION ® F | A | 0.8 |
| CERALUTION ® H | O | 0.65 |
| BIOBASE ® EP | O | 0.15 |
| Ceteareth-20 | O | 1.6 |
| GLYDANT PLUS ® | A | 0.1 |
| Water | A | 47.37 |
| Octinoxate | O | 7.5 |
| Oxybenzone | O | 6 |
| Octisalate | O | 5 |
| Avobenzone | O | 3 |
| Octocrylene | O | 2.5 |
| Acrylates/$C_{12-22}$ alkylmethyl-acrylate copolymer | A | 2.5 |
| Octyldodecyl neopentanoate and/or $C_{12-15}$ alkyl benzoate | O | 5 |
| Triethanolamine | A | 0.3 |
| Acrylates/$C_{10-30}$ alkyl acrylate crosspolymer and/or microcrystalline cellulose and cellulose gum | A | 1.1 |
| Disodium EDTA | A | 0.1 |
| Aloe | A | 0.05 |
| BHT and/or | O | 0.1 |

TABLE 6-continued

Spray Sunscreen Composition

| Emulsion Base | Phase (Aqueous or Oil) | Weight % of Composition |
|---|---|---|
| tocopheryl acetate | | |
| GLYDANT PLUS ® | A | 0.3 |
| TOTAL: | | 100 |

An example of a lotion sunscreen composition formulated with an emulsion base of the present invention is set forth in Table 7.

TABLE 7

Lotion Sunscreen Composition

| Emulsion Base | Phase (Aqueous or Oil) | Weight % of Composition |
|---|---|---|
| Water | A | 14.345 |
| Glycerin | A | 1.2 |
| Lauryl glucoside | A | 1.225 |
| Sodium Lauroyl Sarcosinate | A | 0.48 |
| CERALUTION ® H | O | 0.65 |
| BIOBASE ® EP | O | 0.15 |
| PEG-7 methyl ether | O | 3 |
| Xanthan gum | A | 0.05 |
| EUXYL ® K727 | A | 0.2 |
| Water | A | 51 |
| Octinoxate | O | 7.5 |
| Octisalate | O | 5 |
| Octocrylene | O | 1.2 |
| Oxybenzone | O | 3 |
| Avobenzone | O | 1.5 |
| Di-PPG-3 myristyl ether adipate and/or LEXFEEL 350 | O | 3 |
| Tribehenin | O | 2 |
| Glyceryl Stearate | O | 2 |
| Octadecene/MA copolymer | O | 1.5 |
| CARBOPOL ULTREZ 21 and/or xanthan gum | A | 0.6 |
| Trisodium EDTA | A | 0.1 |
| Triethanolamine | A | 0.3 |
| TOTAL: | | 100 |

LEXFEEL 350, which is dipentaerythritol hexa $C_{5-9}$ acid esters, is available from Inolex.
CARBOPOL ULTREZ 21, which is acrylates/$C_{10-30}$ alkyl acrylate crosspolymer, is available from Noveon.

Another example of a lotion sunscreen composition formulated with an emulsion base of the present invention is set forth in Table 8.

TABLE 8

Lotion Sunscreen Composition

| Emulsion Base | Phase (Aqueous or Oil) | Weight % of Composition |
|---|---|---|
| Water | A | 14.345 |
| Glycerin | A | 1.2 |
| Lauryl glucoside | A | 1.225 |
| Sodium Lauroyl Sarcosinate | A | 0.48 |
| CERALUTION ® H | O | 0.65 |
| BIOBASE ® EP | O | 0.15 |
| PEG-7 methyl ether | O | 5 |
| Xanthan gum | A | 0.05 |
| GLYDANT ® PLUS | A | 0.3 |
| Water | A | 50.2 |
| Octinoxate | O | 7.5 |
| Octisalate | O | 5 |
| UV TITAN X263 | O | 4 |
| Di-PPG-3 myristyl ether adipate and/or LEXFEEL 350 | O | 3 |
| Glyceryl stearate | O | 2 |
| Tribehenin | O | 2 |
| Octadecene/MA copolymer | O | 1.5 |
| Triethanolamine | A | 0.7 |
| CARBOPOL ULTREZ 21 and/or xanthan gum | A | 0.6 |
| Trisodium EDTA | A | 0.1 |
| TOTAL: | | 100 |

UV TITAN X263 is available from Kemira and includes titanium dioxide, alumina, sodium hexametaphosphate, and polyvinylpyrrolidone (PVP).

Yet another example of a lotion sunscreen composition formulated with an emulsion base of the present invention is set forth in Table 9.

TABLE 9

Lotion Sunscreen Composition

| Emulsion Base | Phase (Aqueous or Oil) | Weight % of Composition |
|---|---|---|
| Water | A | 11.2 |
| Glycerin | A | 1.2 |
| PEMULEN ® TR-2 | A | 0.1 |
| Sodium Lauroyl Sarcosinate | A | 0.3 |
| CERALUTION ® H | O | 0.65 |
| BIOBASE ® EP | O | 0.15 |
| PEG-7 methyl ether | O | 4 |
| Xanthan gum | A | 0.05 |
| EUXYL ® K727 | A | 0.2 |
| Water | A | 49.2 |
| Octinoxate | O | 7.5 |
| Octisalate | O | 5 |
| Homosalate | O | 7 |
| UV TITAN M263 | O | 4 |
| Xanthan gum and/or CARBOPOL ULTREZ 21 | A | 0.45 |
| Trisodium EDTA | A | 0.1 |
| Triethanolamine | A | 0.4 |
| ALLIANZ OPT | A | 2.5 |
| Di-PPG-3 myristyl ether adipate and/or LEXFEEL 350 | O | 2 |
| Tribehenin and/or cetyl palmitate | O | 4 |
| TOTAL: | | 100 |

ALLIANZ OPT, which is an acrylates/$C_{12-22}$ alkylmethylacrylate copolymer, is available from ISP.

The following is an example of a spray composition having an emulsion base of the present invention.

TABLE 10

Sunblock Lotion

| Emulsion Base | Phase (Aqueous or Oil) | Weight % of Composition |
|---|---|---|
| Water | A | 15.7 |
| Glycerin | A | 1.2 |
| PEMULEN ® TR-2 | A | 0.1 |
| Sodium Lauroyl Sarcosinate | A | 0.3 |
| CERALUTION ® H | O | 0.65 |
| BIOBASE ® EP | O | 0.15 |
| LEXGARD ® O | O | 2 |
| Xanthan gum | A | 0.05 |
| EUXYL ® K727 | A | 0.2 |
| Water | A | 54.75 |
| Octinoxate | O | 1.2 |
| Octisalate | O | 5 |
| Homosalate | O | 8 |
| Avobenzone | O | 1.5 |
| Oxybenzone | O | 3 |
| Xanthan gum and/or CARBOPOL ULTREZ 21 | A | 0.6 |
| CRODAMOL PMP | O | 3 |
| Trisodium EDTA | A | 0.1 |
| Triethanolamine | A | 0.5 |
| ALLIANZ OPT | A | 2 |
| TOTAL: | | 100 |

CRODAMOL PMP is a PPG-2 Myristyl Ether Propionate, and is available from Croda.

The following is an example of a sunblock lotion composition having an emulsion base of the present invention.

TABLE 11

Sunblock Lotion

| Emulsion Base | Phase (Aqueous or Oil) | Weight % of Composition |
|---|---|---|
| Water | A | 15.7 |
| Glycerin | A | 1.2 |
| PEMULEN ® TR-2 | A | 0.1 |
| Sodium Lauroyl Sarcosinate | A | 0.3 |
| CERALUTION ® H | O | 0.65 |
| BIOBASE ® EP | O | 0.15 |
| LEXGARD ® O | O | 1.5 |
| Xanthan gum | A | 0.05 |
| EUXYL ® K727 | A | 0.2 |
| Water | A | 52.25 |
| Octinoxate | O | 1.2 |
| Octisalate | O | 5 |
| Homosalate | O | 8 |
| Avobenzone | O | 1.5 |
| Oxybenzone | O | 3 |
| Xanthan gum and/or CARBOPOL ULTREZ 21 | A | 0.6 |
| CRODAMOL STS | O | 3 |
| Disodium EDTA | A | 0.1 |
| Tribehenin and/or stearyl Alcohol | O | 3 |
| Triethanolamine | A | 0.5 |
| ALLIANZ OPT | A | 2 |
| TOTAL: | | 100 |

The following is an example of a sunblock lotion composition having an emulsion base of the present invention.

TABLE 12

Sunblock Lotion

| Emulsion Base | Phase (Aqueous or Oil) | Weight % of Composition |
|---|---|---|
| Water | A | 15.7 |
| Glycerin | A | 1.2 |
| PEMULEN ® TR-2 | A | 0.1 |
| Sodium Lauroyl Sarcosinate | A | 0.3 |
| CERALUTION ® H | O | 0.65 |
| BIOBASE ® EP | O | 0.15 |
| LEXGARD ® 0 | O | 1.5 |
| Xanthan gum | A | 0.05 |
| EUXYL ® K727 | A | 0.2 |
| Water | A | 48.95 |
| Octinoxate | O | 1.2 |
| Octisalate | O | 5 |
| Homosalate | O | 8 |
| Avobenzone | O | 1.5 |
| Oxybenzone | O | 3 |
| Xanthan gum and/or CARBOPOL ULTREZ 21 | A | 0.6 |
| PEG-7 Methyl Ether | O | 3 |
| Tribehenin and/or cetyl Alcohol and/or stearyl Alcohol | O | 3.3 |
| CRODAMOL PMP | O | 3 |
| Disodium EDTA | A | 0.1 |
| Triethanolamine | A | 0.5 |
| ALLIANZ OPT | A | 2 |
| TOTAL: | | 100 |

Having thus described the present invention with particular reference to preferred embodiments thereof, it will be apparent that various changes and modifications may be made therein without departing from the spirit and scope of the present invention.

What is claimed is:

1. A stable composition comprising an emulsion base, the emulsion base comprising:
   one or more primary surfactants comprising the combination of sodium dicocoylethylenediamine polyethyleneglycol-15 sulfate and sodium lauroyl sulfate;
   two co-surfactants, wherein said two co-surfactants are the combination of behenyl alcohol, glyceryl stearate, glyceryl stearate citrate, and sodium dicocoylethylenediamine PEG-15 sulfate, and the combination of glyceryl stearate, cetearyl alcohol, sodium lauroyl lactylate, and lecithin;
   a diluent present in an amount of 39 wt. % to 87 wt. % of the total weight of the emulsion base;
   an emollient present in an amount of 14 wt. % to 45 wt. % of the total weight of the emulsion base,
   a humectant present in an amount of 3 wt. % to 11 wt. % of the total weight of the emulsion base; and
   a thickener present in an amount from 0.05 wt. % to 3 wt. % of the total weight of the emulsion base,
   wherein the one or more primary surfactants to the two co-surfactants are present in a ratio from 1:3.75 to 3.75:1,
   wherein the emulsion base is 15 wt. % to 25 wt. % of the total weight of the composition.

2. The composition of claim 1, wherein the ratio of the one or more primary surfactants to the two co-surfactants is 3:1.

3. The composition of claim 1, wherein the ratio of the one or more primary surfactants to the two co-surfactants is 1:2.67.

4. The composition of claim 1, wherein the emulsion base further comprises a preservative, wherein the preservative is present in an amount about 0.1 wt. % to about 2 wt. % of the total weight of the emulsion base.

5. The composition of claim 1, wherein the emulsion base further comprises one or more ingredients selected from the group consisting of a sunscreen agent, a secondary surfactant, a secondary emollient, a skin-feel additive, a moisturizing agent, a film former/waterproofing agent, a bio-active ingredient, a pharmaceutical ingredient, a pH adjuster/chelating agent, a secondary preservative, an antimicrobial, a secondary humectant, a rheology modifying agent, a fragrance, a colorant; a plant extract, an absorbent, salicylic acid, alpha and beta hydroxy acid, a vitamin, and any combinations thereof.

6. The composition of claim 1, wherein the ratio of the one or more primary surfactants to the two co-surfactants is 2.13:1.

7. The composition of claim 6, wherein the ratio of the one or more primary surfactants to the two co-surfactants is from 1:2.67 to 3:1.

8. The composition of claim 6, further comprising one or more film former/waterproofing agents.

9. The composition of claim 8, wherein the one or more film former/waterproofing agents to the one or more primary surfactants and two co-surfactants are in the ratio of 0.1:7 to 7:0.1 in the composition.

10. The composition of claim 6, further comprising one or more sunscreen agents.

11. The composition of claim 10, wherein the one or more sunscreens are present at about 1 wt. % to about 40 wt. % of the total weight of the composition.

12. The composition of claim 6, further comprising one or more secondary rheology modifying agents in an amount about 0.01 wt. % to about 10 wt. % of the total weight of the composition.

13. The composition of claim 6, further comprising one or more secondary diluents in an amount about 40 wt. % to about 90 wt. % of the total weight of the composition.

14. The composition of claim 6, further comprising one or more secondary emollients in an amount about 0.1 wt. % to about 30 wt. % of the total weight of the composition.

15. The composition of claim 6, further comprising an effective amount of a pH adjuster to adjust the pH of the compositions to about 3 to about 9.

16. The composition of claim 6, wherein said one or more primary surfactants further comprises sodium lauroyl sarcosinate.

17. The composition of claim 10, further comprising a sunscreen booster.

18. The composition of claim 6, wherein the diluent is water.

19. The composition of claim 6, wherein the emollient is selected from the group consisting of $C_{12}$-$C_{15}$ alkyl benzoate, PEG-7 methyl ether, and a combination thereof.

20. The composition of claim 6, wherein the thickener is selected from the group consisting of acacia gum, xanthan gum, and a combination thereof.

21. The composition of claim 6, wherein the humectant is glycerin.

* * * * *